(12) United States Patent
Lundgren et al.

(10) Patent No.: US 6,660,279 B2
(45) Date of Patent: Dec. 9, 2003

(54) STABILITY FOR INJECTION SOLUTIONS

(75) Inventors: Anna Lundgren, Göteborg (SE); Mats Sundgren, Kållered (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 10/347,046

(22) Filed: Jan. 17, 2003

(65) Prior Publication Data

US 2003/0190310 A1 Oct. 9, 2003

Related U.S. Application Data

(63) Continuation of application No. 09/423,185, filed as application No. PCT/SE99/01440 on Aug. 24, 1999, now Pat. No. 6,576,245.

(30) Foreign Application Priority Data

Sep. 1, 1998 (SE) ................................. 9802938

(51) Int. Cl.⁷ .................................. A61K 9/08
(52) U.S. Cl. ....................................... 424/400; 424/422
(58) Field of Search .................................. 424/400, 422

(56) References Cited

FOREIGN PATENT DOCUMENTS

| EP | 0390244 | | 10/1990 |
|---|---|---|---|
| WO | 9311152 | | 6/1993 |
| WO | 9429336 | | 12/1994 |
| WO | WO 9601275 | * | 1/1996 |
| WO | 9633216 | | 10/1996 |
| WO | 9702284 | | 1/1997 |
| WO | 9723499 | | 7/1997 |
| WO | 9739770 | | 10/1997 |

* cited by examiner

*Primary Examiner*—Carlos Azpuru
(74) *Attorney, Agent, or Firm*—White & Case LLP

(57) ABSTRACT

A primary package containing a low molecular weight peptide-based thrombin inhibitors which package is sealed with a rubber stopper or plunger containing bromobutyl rubber.

14 Claims, No Drawings

STABILITY FOR INJECTION SOLUTIONS

This application is a continuation of U.S. patent application Ser. No. 09/423,185, filed Nov. 3, 1999, now U.S. Pat. No. 6,576,245, which is a §371 of international patent application PCT/SE99/01440, filed Aug. 24, 1999.

FIELD OF THE INVENTION

The present invention relates to solutions of low molecular weight thrombin inhibitors stored in primary packages containing rubber components, such as vials, bottles, cartridges and prefilled syringes. The invention also relates to the medical use of such stored thrombin inhibitor solutions.

BACKGROUND OF THE INVENTION

Solutions for parentheral use of pharmaceutically active substances are normally stored in primary packages such as, vials, bottles, cartridges or in prefilled syringes. The primary packages are sealed by a rubber stopper or plunger. A commonly used rubber material contains chlorobutyl. Solutions of low molecular weight thrombin inhibitor stored in vials, bottles, cartridges and prefilled syringes sealed by a stopper or plunger containing chlorobutyl rubber exhibits increased degradation, leading to shortened time of storage.

DISCLOSURE OF THE INVENTION

It has now surprisingly been found that by using rubber material containing bromobutyl instead of chlorobutyl, the stability of the low molecular weight thrombin inhibitors in solution can be considerably improved.

The present invention provides a primary package, such as a vial, a bottle, a cartridge or a prefilled syringe containing a solution of a low molecular weight thrombin inhibitor for parentheral injection, sealed by a rubber stopper or plunger containing bromobutyl rubber instead of chlorobutyl rubber.

The present invention further provides a medical use of such thrombin inhibitor, or salts of such thrombin inhibitor, solutions kept in a primary package as mentioned above sealed by bromobutyl stoppers or plungers.

The present invention further provides an aqueous solution for parenteral administration comprising a low molecular weight peptide-based thrombin inhibitor o a salt thereof, having a pH in the range 3 to 8, preferably a pH about 5 and stored in a primary package, such as a vial, a bottle, a cartridge or a prefilled syringe, sealed by a rubber stopper or plunger containing bromobutyl.

Thrombin inhibitors referred to in this application are low molecular weight peptide-based thrombin inhibitors. The term "low molecular weight peptide-based thrombin inhibitors" will be well understood by one skilled in the art to include thrombin inhibitors with one to four peptide linkages, and/or with a molecular weight below 1000, and includes those described generically and, more preferably, specifically in the review paper by Claesson in Blood Coagul. Fibrin (1994)5, 411, as well as those disclosed in U.S. Pat. No. 4,346,078; International Patent Applications WO 97/23499, WO 97/02284, WO97/46577, WO 98/01422, WO 93/05069, WO93/11152, WO 95/23609, WO95/35309, WO 96/25426, WO 94/29336, WO WO 93/18060 and WO 95/01168; and European Patent Applications 623 596, 648 780, 468 231, 559 046, 641 779, 185 390, 526 877, 542 525, 195 212, 362 002, 364 344, 530 167, 293 881, 686 642, 669 317 and 601 459.

Preferred low molecular weight peptide-based thrombin inhibitors include those known collectively as the "gatrans".

Particular gatrans which may be mentioned include HOOC—$CH_2$(R)Cha-Pic-Nag-H (known as inogatran; see International Patent Application WO 93/11152 and the list of abbreviations therein) and HOOC—$CH_2$—(R)Cgl-Aze-Pab-H (known as melagatran; see International Patent Application WO 94/29336 and the list of abbreviations therein).

The preferred low molecular weight peptide-based thrombin inhibitor to be kept in glass vials or syringes is selected from the group consisting of inogatran, (Glycine, N-[2-[2-[[[3-[(aminoimino-methyl)amino]propyl]amino]carbonyl]-1-piperidinyl]-1-(cyclohexylmethyl)-2-oxyethyl]-, [2R-[2S]]-), melagatran, (Glycine, N-[2-[2-[[[4 (aminoiminomethyl)phenyl]-methyl]amino]carbonyl]-1-azetidinyl]-1-cyclohexyl-2-oxoethyl]-, [2R-[2S]]-) and compound A, (Glycine, N-[1-cyclohexyl-2-[2-[[[4-[(hydroxyimino)aminomethyl]-phenyl]methyl]amino] carbonyl]-1-azetidinyl]-2-oxoethyl]-, ethyl ester, [S-(R*, S*)]-).

In one embodiment of the invention the thrombin inhibitor (preferably melagatran) solutions for parentheral injection is a water solution and are kept in primary packages such as vials, bottles, cartridges or prefilled syringes having a rubber stopper or plunger containing a bromobutyl.

In another embodiment of the invention; the thrombin inhibitor for parentheral injection is in a water solution with an addition of hydroxy-propyl-β-cyclodextrin (HPβCD). The concentration of the thrombin inhibitor is in the range 0.001–100 mg/ml, preferably 2.5 20 mg/ml.

WORKING EXAMPLE

Analytical Technique
Liquid Chromatography (LC), for All Analysis

The following equipment and parameters were used at the analysis (if melagatran in solution.

| | |
|---|---|
| Flowrate | 1.0 ml/min |
| Wavelength | 237 nm |
| Injection volume | 20 μl |
| Analytical column | Waters Symmetry C8, 150 × 3.9 mm |
| Guard column | Waters Symmetry C8, 22 × 3.9 mm |
| Mobile phase | 20% (v/v) acetonitrile in phosphate buffer, pH 2.0 with 4.6 mM octanesulphonic acid. |

Evaluation

Results in tables are presented as total degradation of melagatran. This means that all by-products are included and presented as area % of melagatran.

Example 1

This example shows a comparison of melagatran in HPβCD-solution in prefilled syringes (1.0 ml) having rubber plungers containing bromobutyl and chlorobutyl, respectively. The syringes were stored at 4, 25 and 50° C. for up to 6 months. The melagatran solution was in direct contact with the different rubber materials.
Manufacturing of Samples
Melagatran, 2.5 mg/ml, in HPβCD Water Solution (40% w/w), pH about 5
Batch HF 839-2601

| | |
|---|---|
| Melagatran | 442.1 mg |
| HPβCD | 80.0 g |
| HCl, 1M | qs |

-continued

| | |
|---|---|
| NaOH, 1M | qs |
| water for injection | to 200 g final weight (density 1.145 g/ml) |

Melagatran was dissolved in water in a separate beaker and adjusted to pH 5.06. HPβCD powder was mixed with this solution together with water. The final solution was mixed with a magnetic stirrer until the substance was completely dissolved and pH was finally adjusted to 5.02, and the solution was filtrated with a 0.22 μm sterile filter.
Melagatran, 10 mg/ml, in HPβCD Water Solution (40% w/w), pH about 5
Batch HF 839-2602

| | |
|---|---|
| Melagatran | 1.77 mg |
| HPβCD | 80.0 g |
| HCl, 1M | qs |
| NaOH, 1M | qs |
| water for injection | to 200 g final weight (density 1.145 g/ml) |

Melagatran was dissolved in water in a separate beaker and adjusted to pH 4.88. HPβCD powder was mixed with this solution together with water. The final solution was mixed with a magnetic stirrer until the substance was completely dissolved and pH was finally adjusted to 5.0, and the solution was filtrated with a 0.22 μm sterile filter.
Filling of Syringes (1.0 ml)
Sample A1 (HF 839-2613) 10 mg/ml
    0.5 ml of HF 839-2602 was filled in 1 ml HYPAK® syringes from Becton Dickinson with a black plunger material (PH 701/50 from The West Company) containing chlorobutyl rubber.
Sample B1 (HF 839-2614) 10 mg/ml
    0.5 ml of HF 839-2602 was filled in 1 ml HYPAK® syringes from Becton Dickinson with a grey plunger material (PH 4416/50 from The West Company) containing bromobutyl rubber.
Sample C1 (HF 839-2615) 2.5 mg/ml
    0.5 ml of HF 839-2601 was filled in 1 ml HYPAK® syringes from Becton Dickinson with a grey plunger material (PH 4416/50 from The West Company) containing bromobutyl rubber.
Sample D1 (HF 839-2616) 10 mg/ml
    0.5 ml of HF 839-2602 was filled in 1 ml HYPAK® syringes from Becton Dickinson with a black plunger material (PH 701/50 from The West Company) containing chlorobutyl rubber.
Results of Stability Studies

| Storage time (months) | pH | Temperature (° C.) | Total degradation (area % of melagatran) |
|---|---|---|---|
| Sample A1 (HF 839–2613) 10 mg/ml-Chlorobutyl rubber ||||
| 0 | 5.2 | — | 1.2 |
| 1 | 5.2 | 4 | 1.0 |
| 1 | 5.3 | 50 | 7.4 |
| 3 | 5.1 | 4 | 1.2 |
| 3 | 5.1 | 25 | 4.5 |
| 3 | 5.2 | 50 | 14.9 |
| 6 | 5.1 | 4 | 1.2 |
| 6 | 5.1 | 25 | 3.7 |
| Sample B1 (HF 839–2614) 10 mg/ml-Bromobutyl rubber ||||
| 0 | 5.2 | — | 1.1 |
| 1 | 5.2 | 4 | 1.0 |

-continued

| Storage time (months) | pH | Temperature (° C.) | Total degradation (area % of melagatran) |
|---|---|---|---|
| 1 | 5.2 | 50 | 6.4 |
| 3 | 5.1 | 4 | 1.2 |
| 3 | 5.1 | 25 | 2.4 |
| 3 | 5.2 | 50 | 12.8 |
| 6 | 5.1 | 4 | 1.1 |
| 6 | 5.1 | 25 | 3.1 |
| Sample C1 (HF 839–2615) 2.5 mg/ml-Bromobutyl rubber ||||
| 0 | 5.3 | — | 1.2 |
| 1 | 5.4 | 4 | 1.1 |
| 1 | 5.3 | 50 | 7.2 |
| 3 | 5.3 | 4 | 1.3 |
| 3 | 5.3 | 25 | 3.9 |
| 3 | 5.2 | 50 | 14.2 |
| 6 | 5.2 | 4 | 1.2 |
| 6 | 5.2 | 25 | 5.7 |
| Sample D1 (HF 839–2616) 10 mg/ml-Chlorobutyl rubber ||||
| 0 | 5.3 | — | 1.2 |
| 1 | 5.4 | 4 | 1.2 |
| 1 | 5.3 | 50 | 8.6 |
| 3 | 5.3 | 4 | 1.2 |
| 3 | 5.3 | 25 | 3.1 |
| 3 | 5.2 | 50 | 17.4 |
| 6 | 5.2 | 4 | 1.4 |
| 6 | 5.2 | 25 | 9.9 |

Conclusion

Rubber plungers containing chlorobutyl result in a more pronounced degradation compared to rubber plungers containing bromobutyl. This is true for high concentrations as well as low concentrations of melagatran in aqueous solutions.

The most pronounced difference was seen between plungers of chlorobutyl rubber and bromobutyl rubber when the dose of melagatran in aqueous solution was as low as 2.5 mg/ml.

Example 2

This example is a comparison of melagatran in a water solution of HPβCD and melagatran in a water solution of NaCl. Both solutions are in direct contact with rubber plungers containing bromobutyl.

3 plungers of the quality FM 257 (from Helvoet Pharma N.V.) were placed in each 3 ml glass vial together with 1 ml solution of melagatran (NaCl water solution and HPβCD water solution, respectively). Reference samples, that is melagatran in NaCl water solution and in HPβCD water solution having no contact with plunger material. The reference samples were treated in the same way as the other samples. The vials were stored at 50° C. for up to 3 months.

Compared to the study of Example 1 the ratio between solution exposed plunger surface and the quantity of melagatran solution is 16 times higher.
Manufacturing of Samples
Melagatran, 7.5 mg/ml, in HPβCD Water Solution (40% w/w), pH about 5
Batch HF 839-2679

| | | |
|---|---|---|
| Melagatran | 928.8 | mg |
| HPβCD | 55.0 | g |
| HCl, 1M | qs | |
| NaOH, 1M | qs | |
| water for injection | 137.4 | g (density 1.145 g/ml) |

Melagatran and HPβCD were dissolved in water and adjusted to pH 4.96. The final solution was diluted with water to final weight and sterile filtrated with 0.45 μm filter.

Melagatran, 7.5 mg/ml, in NaCl Water Solution, pH about 5
Batch HF 839-2680

| | |
|---|---|
| Melagatran | 1315.5 g |
| NaCl | 1.441 g |
| HCl, 1M | qs |
| NaOH, 1M | qs |
| water for injection | to 170 (density 1.0 g/ml) |

Melagatran and NaCl were dissolved in water and adjusted to pH 5.03. The final solution was diluted with water to final weight and sterile filtrated with 0.22 µm filter.

Filling of Vials

Sample A2 (HF 839-2682) 7.5 mg/ml in NaCl 1.0 ml of HF 839-2680 was filled in 3 ml vials together with 3 black unsiliconized plungers (FM 257 from Helvoet Pharma N.V.) containing bromobutyl rubber.

Sample B2 (HF 839-2683) 7.5 mg/ml in NaCl 1.0 ml of HF 839-2680 was filled in 3 ml vials together with 3 black siliconized plungers (FM 257 from Helvoet Pharma N.V.) containing bromobutyl rubber.

Sample C2 (HF 839-2684) 7.5 mg/ml in NaCl 1.0 ml of HF 839-2680 was filled in 3 ml vials together with 3 grey siliconized plungers (FM 257 from Helvoet Pharma N.V.) containing bromobutyl rubber.

Sample D2 (HF 839-2688) 7.5 mg/ml in NaCl 1.0 ml of HF 839-2680 was filled in 3 ml vials (Reference).

Sample E2 (HF 839-2689) 7.5 mg/ml in HPβCD 1.0 ml of HF 839-2679 was filled in 3 ml vials together with 3 black unsiliconized plungers (FM 257 from Helvoet Pharma N.V.) containing bromobutyl rubber.

Sample F2 (HF 839-2690) 7.5 mg/ml in HPβCD 1.0 ml of HF 839-2679 was filled in 3 ml vials together with 3 black siliconized plungers (FM 257 from Helvoet Pharma N.V.) containing bromobutyl rubber.

Sample G2 (HF 839-2691) 7.5 mg/ml in HPβCD 1.0 ml of HF 839-2679 was filled in 3 ml vials together with 3 grey siliconized plungers (FM 257 from Helvoet Pharma N.V.) containing bromobutyl rubber.

Sample H2 (HF 839-2695) 7.5 mg/ml in HPβCD 1.0 ml of HF 839-2679 was filled in 3 ml vials (Reference).

Results of Stability Studies

| Storage time (months) | pH | Temperature (° C.) | Total degradation (area % of melagatran) |
|---|---|---|---|
| Sample A2 (HF 839-2682) 7.5 mg/ml in NaCl-Bromobutyl rubber | | | |
| 1 | 5.9 | 50 | 4.2 |
| 3 | 6.0 | 50 | 9.3 |
| Sample B2 (HF 339-2683) 7.5 mg/ml in NaCl-Bromobutyl rubber | | | |
| 1 | 5.8 | 50 | 4.0 |
| 3 | 6.0 | 50 | 8.7 |
| Sample C2 (HF 839-2684) 7.5 mg/ml in NaCl-Bromobutyl rubber | | | |
| 1 | 5.8 | 50 | 3.7 |
| 3 | 5.8 | 50 | 7.9 |
| Sample D2 (HF 839-2688) 7.5 mg/ml in NaCl-Reference | | | |
| 1 | 5.2 | 4 | 1.4 |
| 3 | 5.3 | 4 | 1.4 |
| 1 | 5.4 | 50 | 3.4 |
| 3 | 5.6 | 50 | 6.8 |

| Storage time (months) | pH | Temperature (° C.) | Total degradation (area % of melagatran) |
|---|---|---|---|
| Sample E2 (HF 839-2689) 7.5 mg/ml in HPβCD-Bromobutyl rubber | | | |
| 1 | 5.5 | 50 | 5.5 |
| 3 | 5.6 | 50 | 11.3 |
| Sample F2 (HF 839-2690) 7.5 mg/ml in HPβCD-Bromobutyl rubber | | | |
| 1 | 5.4 | 50 | 5.4 |
| 3 | 5.5 | 50 | 11.3 |
| Sample G2 (HF 839-2691) 7.5 mg/ml in HPβCD-Bromobutyl rubber | | | |
| 1 | 5.4 | 50 | 5.4 |
| 3 | 5.5 | 50 | 10.3 |
| Sample H2 (HF 839-2695) 7.5 mg/ml in HPβCD-Reference | | | |
| 1 | 5.2 | 4 | 1.5 |
| 3 | 5.3 | 4 | 1.7 |
| 1 | 5.3 | 50 | 5.7 |
| 3 | 5.4 | 50 | 10.7 |

Conclusion

Melagatran in a water solution of NaCl exhibits a somewhat lower degradation compared to melagatran in a water solution of HPβCD. This is true both for solutions in contact with plunger material (FM 257 bromobutyl) 8%* compared to 11%*, and solutions in absence of plunger material (reference) 7%* compared to 11%*.

*, is total degradation in area % of melagatran

Example 3

This example shows a comparison of different kinds of stopper and plunger materials containing either bromobutyl rubber or chlorobutyl rubber in contact with a melagatran solution (NaCl, pH 5). Melagatran solution was filled in glass vials (3 ml) together with stoppers and plungers of different brands. 5 different rubber materials were used in the study. There were 3 different bromobutyl and 2 different chlorobutyl rubbers. As reference, NaCl water solution of melagatran was stored without any contact with stopper or plunger material.

The ratio between exposed plunger or stopper surface and melagatran in water solution is higher than in example 1. A calculation has been made of exposed area of each tested plunger or stopper material. In the study the area ratio is 10–15 times higher compared to the area represented in Example 1. The vials were studied up to 19 days at a temperature of 50° C.

Manufacturing of Samples

Melagatran, 5 mg/ml, in Isotonic NaCl Solution, pH about 5

Batch HF 839-2719

| | |
|---|---|
| Melagatran | 10.0 mg |
| NaCl | 17.6 g |
| HCl, 1M | qs |
| NaOH, 1M | qs |
| water for injection | To 2000 g final weight (density 1.0 g/ml) |

Melagatran and NaCl were dissolved in water and pH adjusted to 4.95. The solution was diluted to final weight with water.

Filling of Vials

The total contact surface between the rubber material and the solution was enhanced in different ways and different extent. One way was by putting pieces of vial stopper material into each vial. For sample A3, the stopper material was divided into eight equal parts, and two parts in each vial (total of 2/8). Another way to enhance the contact surface was to put 2–3 plungers in each vial. For sample E3, three plungers were put in each vial. In samples A3 to F3, the contact surface was increased of 10–15 times compared to the normal contact surface between plunger and solution in a 1 ml syringe (used in Example 1).

Sample A3 (HF 839-2727) 5 mg/ml in NaCl
  1.5 ml of HF 839-2719 was filled in a 3 ml vial together with two 1/8 parts of a 10 ml vial stopper (FM 50 from Helvoet Pharma N.V.) containing chlorobutyl rubber.

Sample B3 (HF 839-2728) 5 mg/ml in NaCl
  1.5 ml of HF 839-2719 was filled in 3 ml vial together with 2 grey plungers (PH 4023/50 from The West Company) containing bromobutyl rubber.

Sample C3 (HF 839-2729) 5 mg/ml in NaCl
  1.5 ml of HF 839-2719 was filled in 3 ml vial together with 2 black plungers (PH 701/50 from The West Company) containing chlorobutyl rubber.

Sample D3 (HF 839-2730) 5 mg/ml in NaCl
  1.5 ml of HF 839-2719 was filled in 3 ml vial together with 2 grey plungers (W 4416/50 from The West Company) containing bromobutyl rubber.

Sample E3 (HF 839-2731) 5 mg/ml in NaCl
  1.5 ml of HF 839-2719 was filled in 3 ml vial together with 3 black plungers (FM 257 from Helvoet Pharma N.V.) containing bromobutyl rubber.

Sample F3 (HF 839-2732) 5 mg/ml in NaCl
  1.5 ml of HF 839-2719 was filled in 3 ml vial (Reference).

Results of Stability Studies

| Storage time (days) | pH | Temperature (° C.) | Total degradation (area % of melagatran) |
|---|---|---|---|
| Sample A3 (HF 839–2727) 5 mg/ml in NaCl-Chlorobutyl rubber | | | |
| 11 | ~5.0 | 50 | 8.0 |
| 19 | ~5.0 | 50 | 11.8 |
| Sample B3 (HF 839–2728) 5 mg/ml in NaCl-Bromobutyl rubber | | | |
| 11 | ~5.0 | 50 | 0.9 |
| 19 | ~5.0 | 50 | 1.4 |
| Sample C3 (HF 839–2729) 5 mg/ml in NaCl-Chlorobutyl rubber | | | |
| 11 | ~5.0 | 50 | 1.5 |
| 19 | ~5.0 | 50 | 2.4 |
| Sample D3 (HF 839–2730) 5 mg/ml in NaCl-Bromobutyl rubber | | | |
| 11 | ~5.0 | 50 | 1.3 |
| 19 | ~5.0 | 50 | 1.6 |
| Sample E3 (HF 839–2731) 5 mg/ml in NaCl-Bromobutyl rubber | | | |
| 11 | ~5.0 | 50 | 1.2 |
| 19 | ~5.0 | 50 | 1.4 |
| Sample F3 (HF 839–2732) 5 mg/ml in NaCl-Reference | | | |
| 11 | ~5.0 | 50 | 0.6 |
| 19 | ~5.0 | 50 | 1.0 |

Conclusion

All three bromobutyl rubber materials demonstrate lower melagatran degradation compared to the two chlorobutyl rubber materials.

Summary Conclusion

It is shown in Example 1 that, for water solutions containing melagatran stored in HYPAK® syringes (from Becton Dickinson), improved stability is demonstrated using plungers containing bromobutyl rubber compared to the corresponding plungers containing chlorobutyl rubber.

It is shown in Example 2 that, for water solutions of melagatran stored in glass vials, improved stability is demonstrated using a NaCl water solution compared to a HPβCD water solution. This is true for melagatran in solution with and without contact of plungers containing bromobutyl rubber.

It is shown in Example 3 that for melagatran in a NaCl water solution, improved stability is demonstrated using rubber materials containing bromobutyl compared to rubber materials containing chlorobutyl.

What is claimed is :

1. An improved method of administering an aqueous solution of a low molecular weight peptide-based thrombin inhibitor or a salt thereof in the treatment of a thrombin-related condition, wherein the improvement comprises containing and administering the solution from a primary package sealed with a stopper or plunger comprising bromobutyl rubber.

2. The method according to claim 1, wherein the primary package is selected from the group consisting of vials, bottles, cartridges, and prefilled syringes.

3. The method according to claim 1, wherein the thrombin inhibitor is a gatran.

4. The method according to claim 1, wherein the thrombin inhibitor is inogartan.

5. The method according to claim 1, wherein the thrombin inhibitor is melagatran.

6. The method according to claim 1, wherein the thrombin inhibitor is glycine, N-[1-cyclohexyl-2-[2-[[[[4-[(hydroxyimino)-aminomethyl]-phenyl]-methyl]-amino]-carbonyl]-1-azetidinyl]-2-oxoethyl]-, ethyl ester, [S-(R*,S*)]-.

7. The method according to claim 1, wherein the solution is administered parenterally.

8. The method according to claim 1, wherein the pH of the solution is in the range of about 3 to 8.

9. The method according to claim 8, wherein the pH of the solution is about 5.

10. The method according to claim 1, wherein the solution further comprises hydroxy-propyl-β-cyclodextrin.

11. The method according to claim 1, wherein the solution further comprises NaCl.

12. The method according to claim 1, wherein the concentration of the thrombin inhibitor in the solution is in the range of 0.001–100 mg/ml.

13. The method according to claim 12, wherein the concentration of the thrombin inhibitor in solution is the range of 2.5–20 mg/ml.

14. The method according to claim 1, wherein the bromobutyl rubber consists of, or corresponds to, the bromobutyl rubber selected from the group consisting of PH 4023/53; W 4416/50; and FM 257.

* * * * *